US005522836A

United States Patent [19]
Palermo

[11] Patent Number: 5,522,836
[45] Date of Patent: Jun. 4, 1996

[54] ELECTROLYTICALLY SEVERABLE COIL ASSEMBLY WITH MOVABLE DETACHMENT POINT

[75] Inventor: Thomas J. Palermo, Menlo Park, Calif.

[73] Assignee: Target Therapeutics, Inc., Fremont, Calif.

[21] Appl. No.: 266,911

[22] Filed: Jun. 27, 1994

[51] Int. Cl.⁶ .................................. A61B 17/00
[52] U.S. Cl. ................... 606/200; 606/108; 623/1
[58] Field of Search .................. 606/1, 27, 28, 606/29, 32, 108, 151, 154, 195, 198, 200, 78; 623/1, 12; 128/898, 899

[56] References Cited

U.S. PATENT DOCUMENTS

| | | |
|---|---|---|
| 3,868,956 | 3/1975 | Alfidi et al. ............. 606/78 |
| 3,888,237 | 6/1975 | Mori . |
| 4,548,206 | 10/1985 | Osborne . |
| 4,739,768 | 4/1988 | Engelson . |
| 4,884,575 | 12/1989 | Sanders . |
| 4,895,168 | 1/1990 | Machek . |
| 4,994,069 | 2/1991 | Ritchart et al. . |
| 5,108,407 | 4/1992 | Geremia et al. ............. 623/12 |
| 5,122,136 | 6/1992 | Guglielmi et al. . |
| 5,150,717 | 9/1992 | Rosen et al. . |
| 5,226,911 | 7/1993 | Chee et al. . |
| 5,250,071 | 10/1993 | Palermo . |

*Primary Examiner*—Stephen C. Pellegrino
*Assistant Examiner*—William W. Lewis
*Attorney, Agent, or Firm*—Morrison & Foerster

[57] ABSTRACT

This invention is an apparatus for creating an endovascular occlusion by the formation of thrombi in arteries, veins, aneurysms, vascular malformations, and arteriovenous fistulas. In particular, the invention is an assembly for electrolytically severing a portion of the endovascular device such as a coil via the use of electrolysis. The vasoocclusive device is introduced through a catheter and is intended to remain at the desired thrombus formation site. The invention further includes a method for the introduction of the device and its electrolytic separation.

10 Claims, 3 Drawing Sheets

ELECTROLYTICALLY SEVERABLE COIL ASSEMBLY WITH MOVABLE DETACHMENT POINT

FIELD OF THE INVENTION

This invention is an apparatus for creating an endovascular occlusion by the formation of thrombi in such vascular locations as arteries, veins, aneurysms, vascular malformations, and arteriovenous fistulas. In particular, the invention is an assembly for electrolytically severing a portion of the endovascular device such as a coil via the use of electrolysis. The vasoocclusive device is introduced through a catheter and is intended to remain at the desired thrombus formation site. The invention further includes a method for the introduction of the device and its electrolytic separation.

BACKGROUND OF THE INVENTION

Approximately 25,000 intracranial aneurysms rupture each year in North America. The primary purpose of treatment for a ruptured intracranial aneurysm is to prevent re-bleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotaxicly reaching an aneurysm with a probe. The wall of the aneurysm is then perforated from the outside and various techniques are used to occlude the interior in order to prevent it from re-bleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by notice.

A still further approach is the least invasive and is additionally described in Guglielmi et al. It is the endovascular approach. In this approach, the interior of the aneurysm is entered by use of a catheter such as those shown in Engelson (Catheter Guidewire), U.S. Pat. No. 4,884,575 and also in Engelson (Catheter for Guidewire Tracking), U.S. Pat. No. 4,739,768. These patents describe devices utilizing guidewires and catheters which allow access to the aneurysm from remote portions of the body. Specifically, by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures, is found in U.S. Pat. No. 4,994,069, to Ritchart et al. There is described a device—typically a platinum/tungsten alloy coil having a very small diameter—which may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in Palermo (U.S. Pat. No. 5,250,071) or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety ways of linking the embolic coil to the pusher guidewire. For instance, the guidewire may be tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

A further variation of the Guglielmi detachable coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

An improvement to the Guglielmi et al. device is described in U.S. patent application Ser. No. 08/147,529 entitled "Electrolytically Severable Joint for Endovascular Embolic Devices". This document describes a sacrificial joint between the conductor core wire and the detachable coil which, because of its electrical and physical configuration, is able to quickly and predictably separate so to improve the reliability and performance of the Guglielmi et al. device.

A continuation-in-part application to Guglielmi et al. '136 discussed above. U.S. Pat. No. 5,354,295, issued Oct. 11, 1994, entitled "Improvements in an Endovascular Electrolytically Detachable Wire and Tip for the Formation of Thrombus in Arteries, Veins, Aneurysms, Vascular Malformations and Arteriovenous Fistulas" describes the use of mechanically detachable embolic devices as well as those which are electrolytically detachable. The embolic devices may be augmented with attached filaments.

Dr. Taki has devised a variation of the Guglielmi detachable coil using a copper link between the guidewire and the coil.

Each of the described devices requires that the coil be of a specific length chosen prior to its introduction into the body. None of the prior art descriptions permit the attending surgeon to select a device length during the course of introducing the endovascular device into the body.

SUMMARY OF THE INVENTION

This invention is a device for forming a vascular occlusion at a selected site. Generally, the device comprises an electrode placed either on the distal end of a core wire placed within the vasoocclusive device or on the interior of the delivery catheter. The catheter has a distal tip which distal tip may be introduced into the selected vascular site or cavity. The electrode is joined to the core wire or catheter in such a way that the vascular device may be electrolytically detached by application of a current to the core wire or lead to the electrode or the metallic embolic device. The improvement involves the use of an electrode which electrode is movable in relation to the vasoocclusive coil. The electrode may be moved either by sliding the coil with respect to the electrode found on the core wire (the core wire may be either movable or not) or by moving the coil with respect to an electrode found on the interior of the catheter lumen, or the core wire may be moved with respect to the coil itself. Other variations will be apparent from a reading of the specification.

DESCRIPTION OF THE INVENTION

Figure 1:
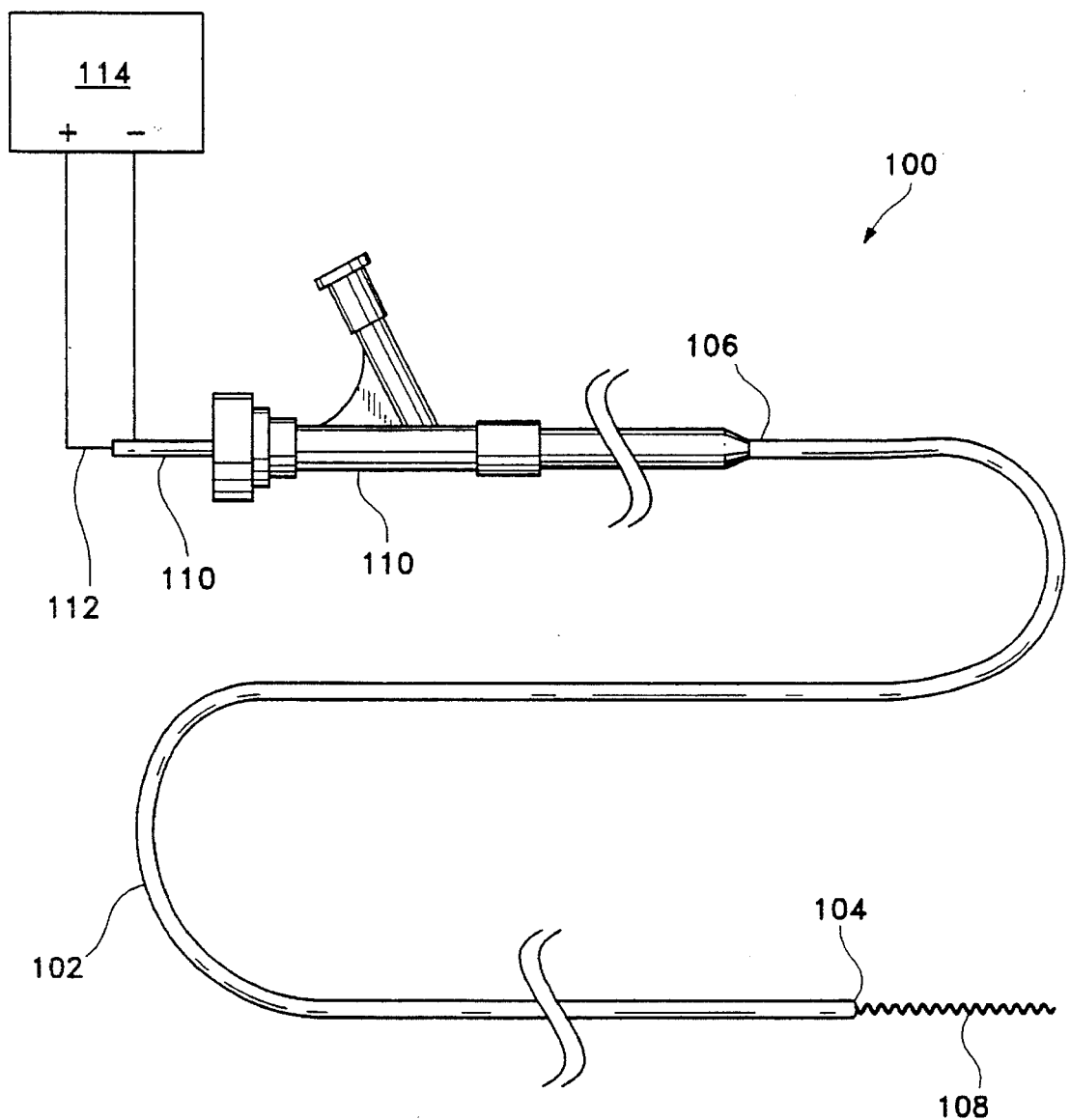
FIG. 1 shows a side view of a generic catheter assembly utilizing the invention.

FIG. 1 shows a side view of a generic catheter assembly (100) made using the inventions described herein. In general, the assembly employs a catheter body (102) which has a distal end (104) and a proximal end (106). The catheter may be of the design noted above in referring to Engelson (U.S. Pat. No. 4,739,768), although it is not critical that such catheter body design be used in this invention. Other catheter bodies are also suitable in various circumstances. Whatever the catheter design, however, there must exist at least one lumen passing between distal end (104) and proximal end (106). Passing through the lumen of catheter body (102) are a collection of components. In particular, detachable coil (108) emanates from distal end (104) as the coil is deployed. A pusher (110) may be used to push the detachable coil (106) from the distal end (104) of the catheter body (102). When used, core wire (112) extends from the catheter body's distal end (106) through pusher (110) and into the center of detachable coil (108). In this configuration, the circuit for electrolytically detaching a desired portion of detachable coil (108) passes through a conductive path found in the pusher (110) and the core wire (112). A small gap desirably is found between the detachable coil (102) and the electrode found on the distal region of the core wire (112). The power supply (114) is found in FIG. 1. In general, we have found that tapered core wires (112) are especially suitable for this inventive procedure and device in that they tend to lessen the friction of the core wire against the various interior parts of the catheter assembly (100). The core wire (112) will typically be covered with an insulating material (as will be discussed in more detail below) with an insulating material such as polyfluorocarbons (e.g., Teflon), polyurethane, polyethylene, polypropylene, or other suitable polymeric material. The electrode, which will also be discussed in more detail below, is not covered with the electrical insulator and is of a material that should not dissolve in the blood upon imposition of the voltage. Indeed, the core wire (112) should, in the region of its distal section, at least, be of a metal which is more noble than that found in the detachable coil (108). The core wire (112) is typically 10–50 mils. in diameter and is of stainless steel or the like. We have found that gold plating the distal tip provides significant resistance to electrolytic disposition. The core wire (112) and, indeed, the entire catheter assembly (100), is typically between 50 and 300 cm. in length. Obviously, the length of the catheter assembly (100) is chosen based upon the use to which the device is to be placed.

Figure 2:
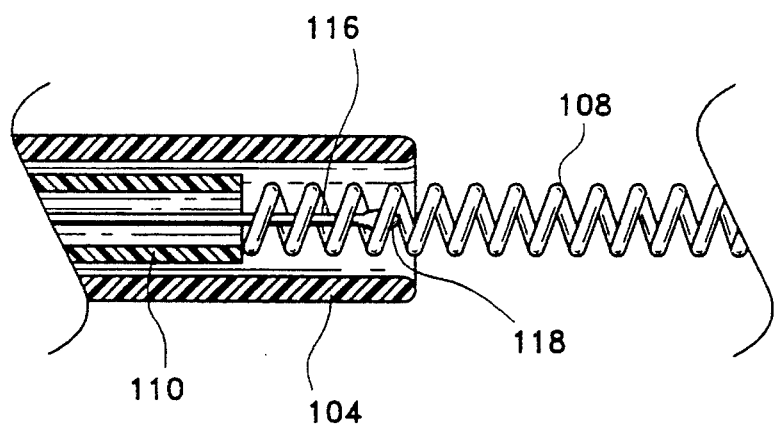
FIGS. 2 and 4 show side-view, partial cross-sectional views of various catheter tips made according to the invention.

FIG. 2 shows one variation of the invention in which the core wire (116) is immobile with respect to the distal end (104) of the catheter body. As was noted above, core wire (116) is coated with an insulator up to the region of the distal electrode (118). Distal electrode (118) is, of course, left uncoated so to allow an electrical path to form through the liquid surrounding it to the detachable coil (108). The pusher (110) is also depicted in FIG. 1. This variation of the device operates in the following fashion. The pusher (110) pushes the detachable coil (108) through the catheter body (104) until the desired length of detachable coil (104) has emanated through the distal end of the catheter lumen. The immobile core wire (116) does not move with respect to catheter body (104). This variation permits the attending physician to understand that the length of the detachable coil (108) which extends beyond the tip of the catheter is the length of detachable coil (108) which will be left at the selected vasoocclusive site.

It should be apparent that the electrode (118) found at the tip of immobile core wire (116) should, at once, be both open to the fluid in the vasculature so to allow the electrolysis to take place but also not be allowed to contact the interior of coil (108) lest a direct short take place. A shroud or protector is desirably placed over the electrode (118). The core wire (116) itself is insulated proximally of the electrode (118).

Preferably such inherently slippery polymers as polyfluorocarbons (such as PTFE, FEP), polysulfones or the like are desirable as such coatings.

Figure 3:
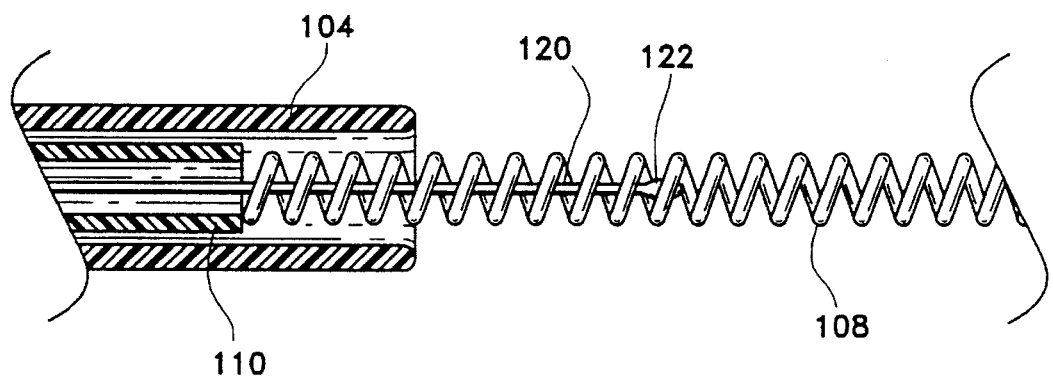

FIG. 3 shows another variation of the invention. As was the case with FIG. 2, the distal end (104) of the catheter body is shown as is pusher (110). In this instance, the detachable coil (108) may be electrolytically severed outside of the catheter body distal tip (104). This is accomplished by use of a movable core wire (120) By "movable" we mean that it may be axially moved within the inner lumen of coil (108) and with respect to the distal tip of (104) of catheter body. This variation clearly allows the attending physician to trim the length of detachable coil (108) at some determinable point outside of the catheter. This may be desirable, for instance, when occluding an aneurysm. In this way, the distal tip of (104) of the catheter body is positioned near the opening of the aneurysm, the proper length of detachable coil (108) is then placed through the mouth of the aneurysm into the sac, and the electrode (122) on core wire (120) is then inserted just into the aneurysm so that during electrolytic dissolution of a small section of the coil, the dissolution takes place within the aneurysm sac beyond the aneurysm neck. This prevents any small sections of coil remaining out in the artery to form other non-desired emboli.

Figure 4:
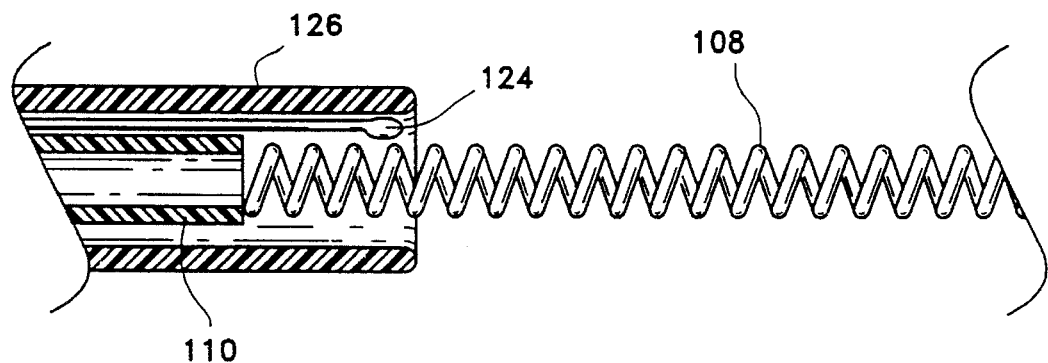

FIG. 4 shows another variation of the inventive device in which no core wire is used. As was the case with the variations shown in FIGS. 2 and 3, the device employs a pusher (110) and a detachable coil (108). However, in lieu of the electrode found interior to the detachable coil (108) found in FIGS. 2 and 3, the electrode (124) in this variation is found on the interior of catheter distal section (126). This configuration has many of the same benefits as does the variation shown in FIG. 2 in that the attending physician is cognizant of the amount of coil to be left at the desired occluded site because that amount of coil equals that amount seen emanating from the distal tip (126) of the catheter body.

The catheter body in this variation has included within its wall (or otherwise provided for), a conductor which extends from the proximal end of the catheter (106) (in FIG. 1) to the electrode (124). It should be apparent that pusher (110) completes the circuit through the detachable coil (108) either by inclusion of a conductive wire in the wall of the pusher (110) or by a discrete wire passing through the lumen of the pusher. In the variations shown in FIGS. 2 and 3, it is more desirable to place the conductor in the wall of the pusher since in that way, the movement of core wire (116) (in FIG. 2) and core wire (120) (in FIG. 3) is not impeded. In the variation shown in FIG. 4, the conductor associated with the proximal end of detachable coil (108) may either be placed within the wall of pusher (110) or through the lumen found in the midsection. Indeed, in certain short catheter assemblies (100) (in FIG. 1) may be completely metallic. It is within purview of this invention that other means of conducting electricity to the proximal end of the detachable coil (108) are reasonable, but such does not form the core idea of this invention.

As was the case in the variation found in FIG. 3, the electrode (122) should be provided with a protector or shroud to allow the contact of the metallic electrode (122) with blood but not to allow the electrode to contact the interior of coil (108). Also as was the case with immobile core wire (116), the core wire (120) is insulated proximally of the metallic tip (122) preferably with a lubricious polymer.

The detachable coil (108) shown in each of the drawings above is shown to be a coil. Indeed, it may be a coil or it may be some other vasoocclusive form such as a braid or a combination of braids and coils. A coil is desired because it more readily severs electrolytically at a single point. Electrolytic dissolution of multi-fibered braid is complicated by the presence of multiple electrolysis points. The diameter of the wire used in such braid is typically much smaller than would be used in a coil but, again, the dissolution process is inherently more complicated. Additionally, it is within the purview of this invention to cover the vasoocclusive device or connect the vasoocclusive device with fibrous materials. The fibrous materials may be materials which cause the vasoocclusive better to form a thrombus. Fibrous materials such as Dacron and the like are acceptable. Fibrous adjuvants such as found in U.S. patent application No. 07/965,973, to Phelps et al., or in U.S. Pat. No. 5,226,911 to Chee et al. entitled "Vasoocclusion Coil with Attached Fibrous Elements" the entirety of which are incorporated by reference, are acceptable.

Figure 5:
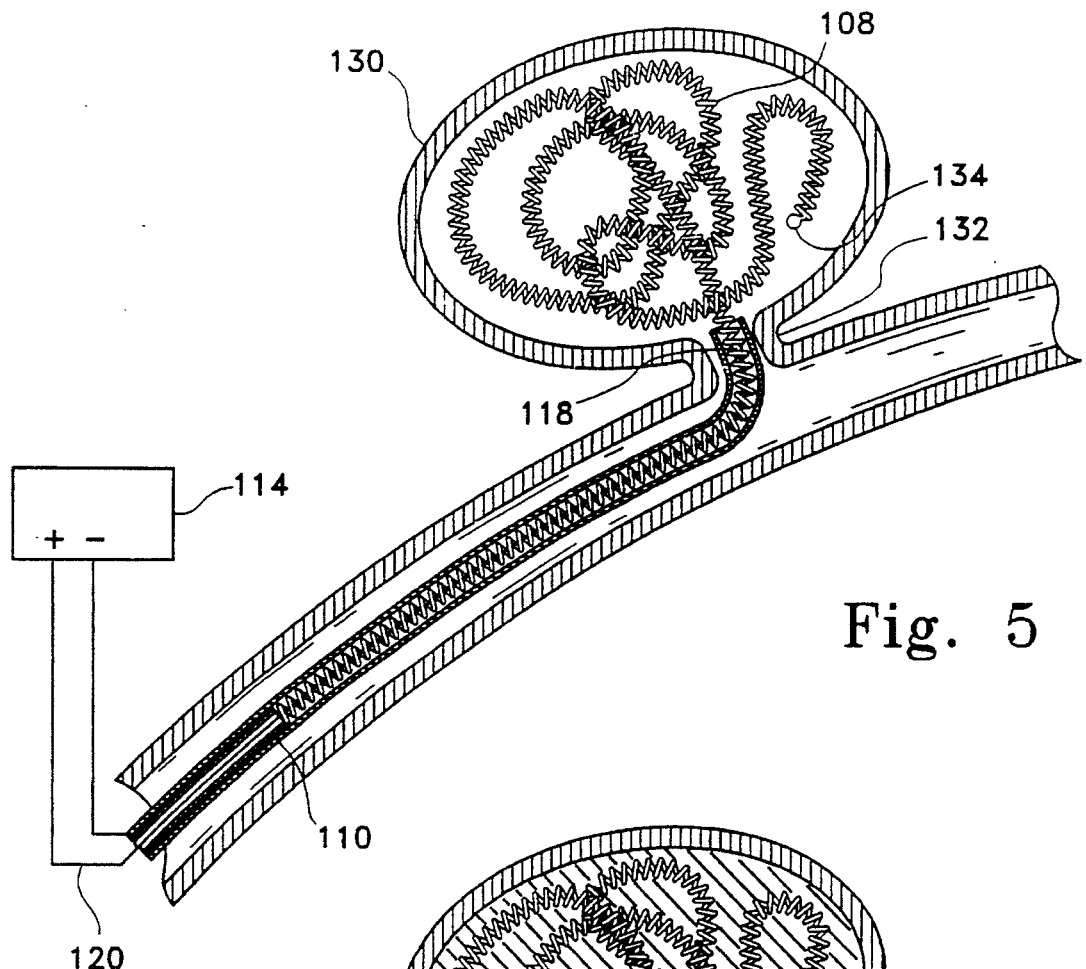
FIGS. 5 and 6 schematically depict a method for deploying the vasoocclusive device.
Figure 6:
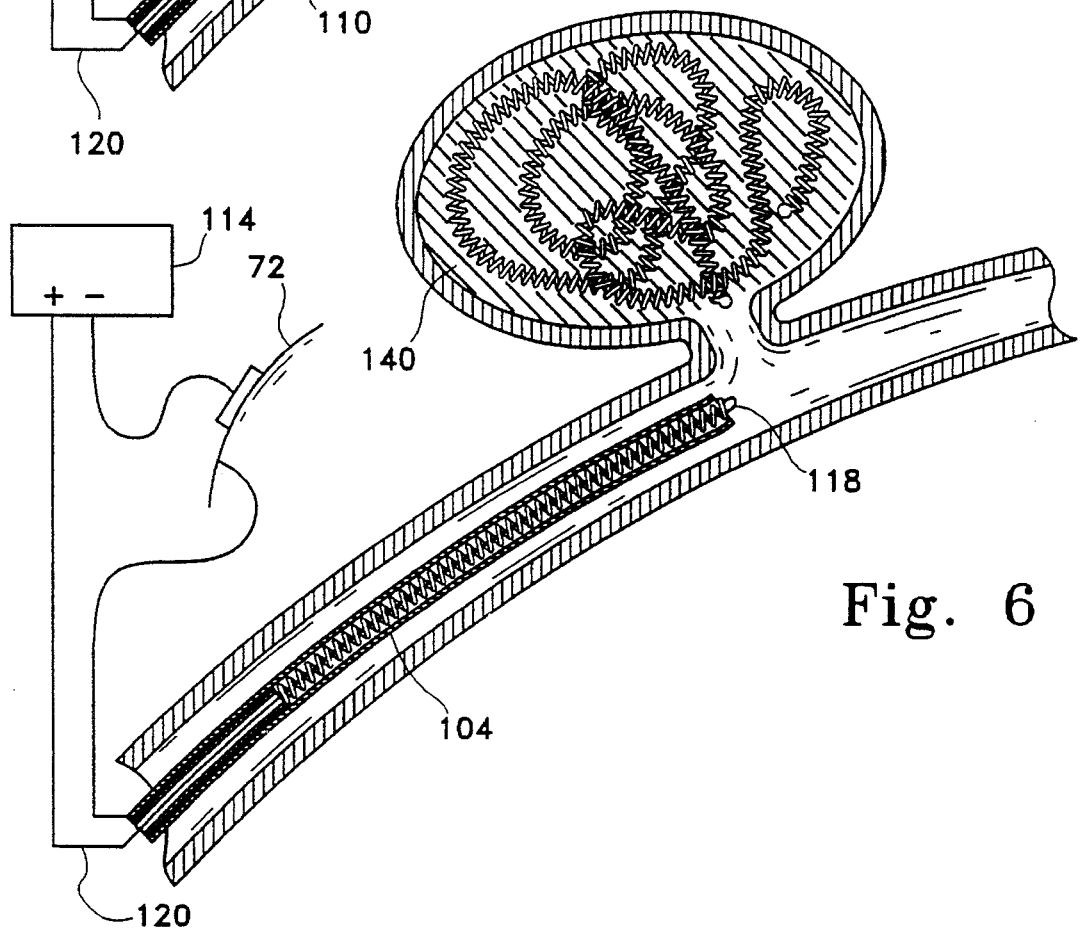

FIGS. 5 and 6 show a typical layout involving the inventive device as was generally described in the Figures above but particularly with regard to FIG. 3. In FIG. 5, a core wire (120) having an electrode (118) at its distal section is coated with an insulation material such as Teflon throughout its length except at the electrode (118). This core wire (120) is placed within pusher (110). As was noted above, the core wire (120) is typically of a diameter of approximately 10–30 mils., although such size is not critical. In the embodiment shown in FIG. 5, the core wire (120) is tapered to its distal end. The vasoocclusive coil (104) is pushed from the catheter into the aneurysm sac (130) through aneurysm neck (132). Preferably, detachable vasoocclusive device (108) when a coil, forms a secondary loop after it leaves the end of the catheter. The most distal end (134) of detachable coil (108) may also have an end plug or tip of some type simply to prevent punctures of the aneurysm as it is introduced into the aneurysm sac. As noted, the detachable coil (108) may be prebiased to form a cylinder or a conical envelope. The coil may be heat treated or crimped or otherwise physically treated to form a random shape after it is ejected from the catheter. It is desirable that a significant volume of the aneurysm be filled with the vasoocclusive device. Consequently, it is desirable that the device be quite flexible so to allow its conformance to the inner wall of the aneurysm without puncture. In any event, once the coil is properly placed within the aneurysm and the attending physician positions the electrode (118)' so to trim a proper amount of the detachable coil (108) into the aneurysm, a modest voltage is then applied to the device. In particular, a positive electric current of approximately 0.1 to 2 milliamps at 0.1 to 5.0 volts is applied to core wire (120) so to form a thrombus within aneurysm sac (130). The negative pole of power supply (114) is attached to the conductor passing through or along the pusher (110).

After the thrombus (140) has been formed (as shown in FIG. 6) and the aneurysm occluded, the core wire (120) with its electrode (118) is withdrawn as is the distal portion of the catheter (104). This removal typically takes place within three to ten minutes, leaving aneurysm sac (132) occluded as is shown in FIG. 6.

The process is typically practiced under fluoroscopic control with local anesthesia. A transfemoral catheter (of which (104) is the distal section) is utilized to treat a cerebral aneurysm. In much heavier patients, the catheter may be introduced into the carotid artery.

Many alterations and modifications may be made by those having ordinary skill in the art without departing from the spirit and scope of this invention. Therefore it must be understood that the concept of electrolytically determining the length of a vasoocclusive device such as described herein is the concept of this invention and may be provided for in a variety of shapes.

The illustrated embodiments have been used only for the purposes of clarity and should not be taken as limiting the invention as defined by the following claims.

I claim as my invention:

1. An assembly for use in conjunction with a delivery catheter in forming a deliverable vasoocclusive device for placement into a mammal vasculature comprising:

(a) a core wire having a proximal end and a distal end and an axis between those ends, which core wire is electrically conductive and has an electrode located distally on said core wire for electrical conduction to a helically wound metallic coil situated coaxially about said core wire in the region of the electrode so to electrolytically disintegrate a portion of the metallic coil in the region of the electrode and upon said disintegration form a severed deliverable vasooclusive device, said core wire being movable axially relative to said metallic coil, and (b) a helically wound metallic coil having a proximal and a distal end and an axis between those ends, severable by electrolysis between said proximal end and said distal end to form a severed deliverable vasoocclusive coil, and situated coaxially about said core wire at least in the region of the core wire electrode.

2. The assembly of claim 1 further comprising an insulative delivery catheter body having a catheter proximal end and a catheter distal end and a catheter body lumen between the catheter distal end and the catheter proximal end and where at least a portion of the coil is situated within said catheter lumen.

3. The assembly of claim 2 where the core wire is fixedly mounted relative to said catheter body lumen.

4. The assembly of claim 3 where the core wire is mounted in the catheter body so that the electrode is open to the distal end of the delivery catheter body lumen.

5. The assembly of claim 2 where the core wire is movable relative to the catheter body.

6. The assembly of claim 5 where the core wire is movable relative to the catheter body so that the electrode may be placed distally of the distal end of the catheter body lumen.

7. The assembly of claim 2 additionally comprising an elongated pusher adapted to fit within said catheter body lumen and to contact said helically wound coil and move said coil distally through said catheter.

8. An assembly for forming a deliverable vasoocclusive coil and for delivering that vasoocclusive coil into a mammal vasculature comprising:

(a) a tubular catheter body having a proximal end and a distal end, a lumen between the proximal and distal ends, and an electrode situated within the catheter lumen in the region of the catheter body distal end for electrolytically disintegrating a portion of a metallic coil in the region of the electrode to form a severed deliverable vasoocclusive coil, and (b) a helically wound metallic coil having a proximal end and a distal end at least partially situated within said catheter body lumen, severable by electrolysis between said proximal end and said distal end to form a severed deliverable vasoocclusive coil, and at least partially movable through the lumen and distally of the distal end of the catheter body for delivery of said severed deliverable vasooclusive coil.

9. The assembly of claim 8 additionally comprising an elongated pusher adapted to fit within said catheter body lumen and to contact said helically wound coil and move said coil distally through said catheter.

10. A method for delivering a selected length of vasoocclusive coil to a chosen site within a mammal vasculature, comprising the steps of:

(a) introducing a catheter having a distal end and a proximal end and a lumen there between into the vasculature to a site where an occlusion is desired, said catheter containing a coil within the lumen thereof, said coil having a length greater than that selected for forming said occlusion and said coil having a distal end and a proximal end, (b) moving an electrode longitudinally relative to the coil until the distance between the distal end of the coil and the electrode equals the selected length for forming said occlusion, and (c) applying a voltage between the electrode and the coil so as to disintegrate at least a portion of the coil in the region of the electrode.

* * * * *

UNITED STATES PATENT AND TRADEMARK OFFICE
CERTIFICATE OF CORRECTION

PATENT NO. : 5,522,836
DATED : June 4, 1996
INVENTOR(S) : Palermo

It is certified that error appears in the above-indentified patent and that said Letters Patent is hereby corrected as shown below:

column 3, line 56: change "and" to --through--.

Signed and Sealed this

Tenth Day of September, 1996

Attest:

BRUCE LEHMAN

Attesting Officer      Commissioner of Patents and Trademarks